US012680039B2

(12) United States Patent
Ibrahem

(10) Patent No.: US 12,680,039 B2
(45) Date of Patent: Jul. 14, 2026

(54) BIOFUEL AND METHOD OF SYNTHESIS OF THE SAME

(71) Applicant: Colabit Sweden AB, Norrsundet (SE)

(72) Inventor: Ismail Ibrahem, Gävle (SE)

(73) Assignee: Colabit Sweden AB, Norrsundet (SE)

( * ) Notice: Subject to any disclaimer, the term of this patent is extended or adjusted under 35 U.S.C. 154(b) by 0 days.

(21) Appl. No.: 18/714,925

(22) PCT Filed: Nov. 30, 2022

(86) PCT No.: PCT/SE2022/051122
§ 371 (c)(1),
(2) Date: May 30, 2024

(87) PCT Pub. No.: WO2023/101592
PCT Pub. Date: Jun. 8, 2023

(65) Prior Publication Data

US 2025/0051669 A1 Feb. 13, 2025

(30) Foreign Application Priority Data

Dec. 1, 2021 (SE) .................................... 2151462-5

(51) Int. Cl.
*C10L 1/02* (2006.01)
*C07C 41/06* (2006.01)
*C10L 10/08* (2006.01)

(52) U.S. Cl.
CPC ................ *C10L 1/02* (2013.01); *C07C 41/06* (2013.01); *C10L 10/08* (2013.01); *C07C 2523/755* (2013.01); *C10L 2200/0446* (2013.01); *C10L 2270/026* (2013.01)

(58) Field of Classification Search
CPC .... C10L 1/02; C10L 10/08; C10L 2200/0446; C10L 2270/026; C10L 2200/0476; C10L 1/026; C10L 1/1852; C07C 41/06; C07C 2523/755; C07C 1/24; C07C 41/09; C07C 43/04; C07C 2/12; C07C 11/02; C07B 33/00; C07B 35/02; C07B 41/04; Y02E 50/10
See application file for complete search history.

(56) References Cited

FOREIGN PATENT DOCUMENTS

| | | | | |
|---|---|---|---|---|
| EP | 0170076 A1 | | 2/1986 | |
| WO | 9213819 A1 | | 8/1992 | |
| WO | 0118154 A1 | | 3/2001 | |
| WO | WO-0118155 A1 | * | 3/2001 | ............ C10L 1/1824 |
| WO | 2011150924 A1 | | 12/2011 | |
| WO | 2017188151 A1 | | 11/2017 | |
| WO | 2018115575 A1 | | 6/2018 | |
| WO | WO-2018115574 A1 | * | 6/2018 | ............ C10L 1/1852 |

OTHER PUBLICATIONS

Numata, M., et al. "Sol-gel preparation of Ni/Ti02 catalysts with bimodal pore structures", Applied Catalysis A: General, 383, May 18, 2010, pp. 66-72.
Discussion of Numata et al. reference by Swedish Examiner in counterpart prosecution, email dated Nov. 18, 2024, 1 page.
International Search Report and Written Opinion for International Application No. PCT/SE2022/051122, mailed Jan. 31, 2023, (19 pages).
Swedish Office Action for Swedish Application No. 2151462-5, mailed Jan. 30, 2023, (9 pages).
Swedish Office Action for Swedish Application No. 2151462-5, mailed Mar. 6, 2024 (6 pages).
Swedish Office Action for Swedish Application No. 2151462-5, mailed May 23, 2022 (12 pages).
Almashhadani et al., "Dehydration of n-propanol and methanol to produce etherified fuel additives," AIMS Energy, vol. 5, pp. 149-162, 2017, (14 pages).
Bailie et al., "Effect of thiophene modification on supported metal catalysts for the hydrogenation of but-2-enal," Journal of Molecular Catalysis A: Chemical 177, pp. 209-214, 2002, (6 pages).

* cited by examiner

*Primary Examiner* — Taiwo Oladapo
(74) *Attorney, Agent, or Firm* — Kagan Binder, PLLC

(57) ABSTRACT

A molecule having a formula (7) for use as a fuel in a combustion engine: and wherein said molecule is a di(2-ethylhexyl) ether.

(7)

7

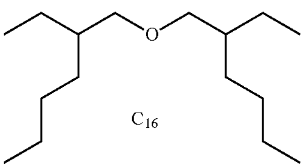

$C_{16}$

6 Claims, No Drawings

BIOFUEL AND METHOD OF SYNTHESIS OF THE SAME

CROSS-REFERENCE TO RELATED APPLICATIONS

This application claims priority to International Application No. PCT/SE2022/051122, filed Nov. 30, 2022 and titled "BIOFUEL AND METHOD OF SYNTHESIS OF THE SAME," which in turn claims priority from a Swedish Patent Application having serial number 2151462-5, filed Dec. 1, 2021, both of which are incorporated herein by reference in their entireties.

TECHNICAL FIELD

The present invention relates to a molecule for use as fuel, or more specifically as biofuel for a combustion engine and a method for production and synthesis of the same.

BACKGROUND

In light of the current need to reduce the greenhouse gas (GHG) emissions in the world, and reduce or eradicated the dependency on fossil fuels there is a need to provide alternative fuel resources. There are a number of different fuels used in combustion engines in for instance the automotive sector, such as petrol, ethanol and diesel. Where petrol and diesel have conventionally been manufactured from petroleum-based sources, i.e. through the refinement of crude oil, there are currently a number of other sources, such as biological material, biomass from the forest i.e. biofuel, and methods for production of these fuels. The use of biofuels is also debated for many reasons, such as that they are not as efficient or actually even as renewable as necessary to cut the GHG emissions.

Ethanol is a simple alcohol and can be easily produced from different types of biomass and can be further manipulated for the employment as biofuel, either directly or through refinement or synthesis into other molecules.

Even though biofuels generally are aimed at mimicking the characteristics of conventional fossil fuels, i.e. with regards to efficiency and function in the engine, there is an increased need to find new types of high value liquid fuels with even more improved qualities.

SUMMARY

It is in view of the above considerations and others that the embodiments described in this disclosure have been made.

This disclosure recognizes the fact that there is a need for new and improved molecules for use as biofuel.

It is an object of the present disclosure, to provide a molecule for use as biofuel and a method for producing the biofuel. The object is wholly achieved by the molecule and inventive method for synthesis of the molecule. The invention is defined by the appended independent claims. Embodiments are set forth in the appended dependent claims and in the following description.

According to a first aspect there is provided a molecule having a general formula 7 for use as a fuel in a combustion engine:

7

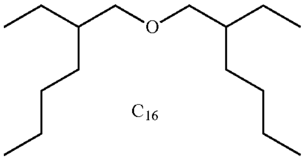

and wherein said molecule is a di(2-ethylhexyl) ether.

The di(2-ethylhexyl) ether, with alternative name: bis(2-ethylhexyl) ether: IUPAC: 3-(((2-ethylhexyl)oxy)methyl) heptane, CAS: 10143-60-9, has previously been used for instance as a lubricant. The invention lies in the surprising finding the di(2-ethylhexyl) ether according to the formula 7 is suitable for use as a fuel in a combustion engine, i.e. as a biofuel molecule.

According to the first aspect the fuel is diesel. The molecule may thus be used as a standalone diesel fuel, i.e. as a higher value liquid fuel.

According to the first aspect the fuel may optionally comprise an additive such as a lubricant.

Further, the fuel according to the first aspect may have a density at 15° C. according to EN ISO 12185 in the range of 800 to 845 kg/m$^3$ or a density at 15° C. according to EN ISO 12185 in the range of 810 to 820 kg/m$^3$, or more preferably a density at 15° C. according to EN ISO 12185 of 814.0 kg/m$^3$.

According to the first aspect the molecule for use as fuel as claimed in any may be mixed with a fossil diesel fuel. Since the biofuel molecule has properties matching a conventional fuel the biofuel molecule may be mixed with a fossil diesel to lower the carbon footprint of the fossil fuel.

According to a second aspect there is provided a one-pot method for producing an intermediary product of the di(2-ethylhexyl) ether according to formula 7,

7

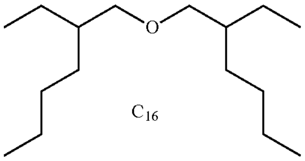

wherein said intermediary product is a branched $C_8$ aldehyde according to the general formula 5,

5

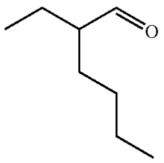

wherein said method comprises an integrated catalytic conversion of a $C_4$ croton aldehyde having the general formula 2:

2

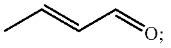

and wherein said method comprises acid catalyzed etherification of a branched $C_8$ alcohol having the general formula 6:

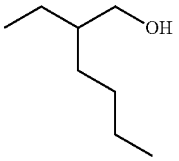

6 through the reaction scheme 2:

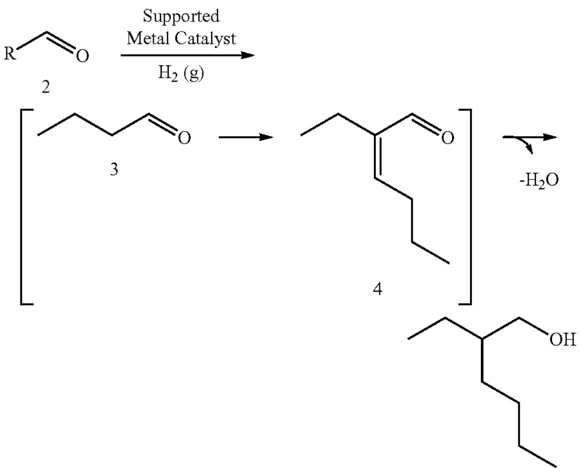

6 in which system a Ni(0) metal catalyst is used.

According to the method of the second aspect there is thus provided a one-pot production method for the di(2-ethylhexyl) ether according to formula 7. In the first step, i.e. the synthesis of the branched alcohol according to formula 6, and by using the Ni(0) metal catalyst, a high ratio of the branched aldehyde according to formula 5 is obtained, which is essential for the subsequent reduction into the intermediate product, i.e. the branched alcohol 6. The desired final product C16 ether is then obtained through an acid catalyzed etherification of branched alcohol 6.

According to a third aspect there is provided a method for the production of a di(2-ethylhexyl) ether according to the formula 7, wherein said is di(2-ethylhexyl) ether is synthesized through an acid catalyzed etherification reaction of the branched $C_8$ alcohol as obtained through the reaction according to any one of the reactions in reaction scheme 6:

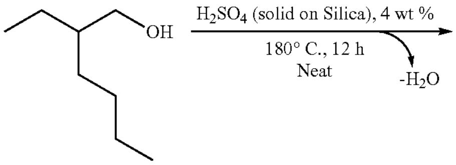

6

-continued

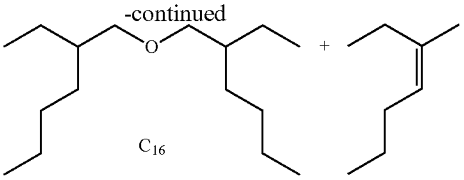

7 13

80:20

99% total conversion

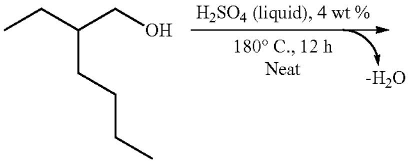

6

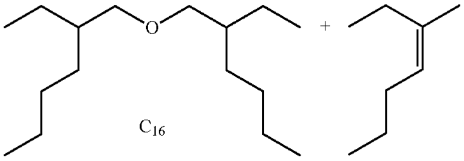

7 13

90:10

99% total conversion .

According to a fourth aspect there is provide a biofuel molecule obtained through the method of the second aspect or the third aspect, having the general formula 7:

7

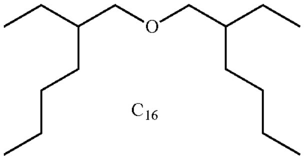

wherein said biofuel molecule is a diesel, and wherein said fuel further has a density at 15° C. according to EN ISO 12185 in the range of 810 to 820 kg/$m^3$ or wherein said fuel has a density at 15° C. according to EN ISO 12185 of 814 kg/$m^3$.

According to a fifth aspect there is provided the use of a molecule having a formula (7) as a fuel in a combustion engine:

7

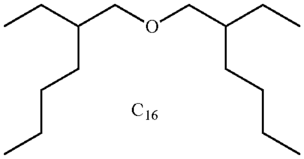

and wherein said molecule is a di(2-ethylhexyl) ether, wherein the fuel has a density at 15° C. according to EN ISO 12185 in the range of 800 to 845 kg/m3 has a density at 15° C. according to EN ISO 12185 of 814

$kg/m^3$. The fuel may have a density at 15° C. according to EN ISO 12185 in the range of 810 to 820 $kg/m^3$, or density at 15° C. according to EN ISO 12185 of 814.0 $kg/m^3$.

According to a sixth aspect there is provided a one-pot method for producing an intermediary product, comprising an integrated catalytic conversion of a $C_4$ croton aldehyde as starting material having the general formula 2, under 10 bar $H_2$, at 100 to 120° C., during 4 hours in a solvent:

2

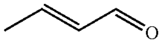

wherein said intermediary product is a branched $C_8$ aldehyde according to the general formula 5, with 100% conversion rate of the starting material based on GC-MS analysis,

5

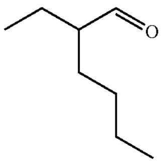

and subsequently reduction of said branched C& aldehyde according to the general formula 5, into the branched alcohol having formula 6:

and wherein said method comprises acid catalyzed etherification of branched $C_8$ alcohol having the general formula 6:

6

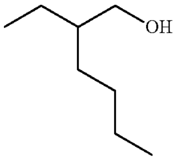

in which reaction a Ni(0) metal or a Pd(0) catalyst is utilized.

According to a seventh aspect there is provided a method for the production of a di(2-ethylhexyl) ether according to the formula 7,

7

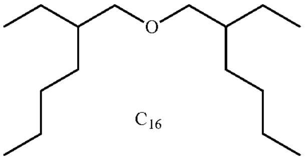

wherein said is di(2-ethylhexyl) ether is synthesized through an acid catalyzed etherification reaction of the branched $C_8$ alcohol according to formula 6 as a starting material:

6

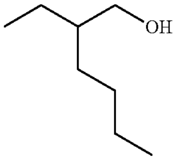

and as obtained through the reaction according to the sixth aspect, according to any one of the following reactions:

reacting compound 6 with 4 wt.-% $H_2SO_4$ solid on silica at 180° C. for 12 h, neat, wherein water is removed, resulting in an 80:20 ratio of compound 7 and compound 13 having formula:

13

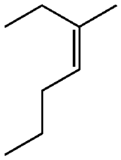

and 99% conversion of said starting material; and/or reacting compound 6 with 4 wt. % $H_2SO_4$ in a liquid at 180° C. for 12 h, neat, wherein water is removed, resulting in a 90:10 ratio of compound 7 and compound 13 and a 99% conversion of said starting material.

According to an eight aspect there is provided the use of a molecule having a formula (7) obtained by the method according to the seventh aspect as a fuel in a combustion engine:

7

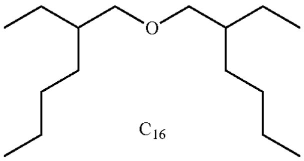

and wherein said molecule is a di(2-ethylhexyl) ether, wherein the fuel has a density at 15° C. according to EN ISO 12185 in the range of 800 to 845 $kg/m^3$ has a density at 15° C. according to EN ISO 12185 of 814 $kg/m^3$.

DESCRIPTION OF EMBODIMENTS

The $C_{16}$ ether, i.e. the di(2-ethylhexyl) ether for use as liquid fuel for a combustion engine, or more specifically as diesel fuel, with the alternative name: Bis(2-ethylhexyl) ether: IUPAC: 3-(((2-ethylhexyl)oxy)methyl)heptane, CAS: 10143-60-9, was synthesized according to a two-step synthesis, where a first step is preferably performed in a so called one-pot method, with a subsequent acid catalyzed etherification in a separate and final step, and will be described in more detail below.

The starting material for the inventive biofuel is preferably a bioethanol, produced from conventional sources, such as biomass. The bioethanol may further be oxidized through conventional methods to acetaldehyde, or converted or croton aldehyde.

A branched $C_8$ alcohol according to formula 6 below, was in a first step prepared by integrated catalytic system from a simple $C_2$ acetaldehyde according to the general formula 1 below or from a $C_4$ croton aldehyde according to the general formula 2 below in a one-pot method. Preferably, the $C_4$ croton aldehyde according to the general formula 2, is used as feedstock and is catalytically transformed into branched saturated aldehyde according to the general formula 5 below, and subsequently reduced into the branched alcohol having formula 6. By using the $C_4$ croton aldehyde a more precis control of the reaction is achieved, i.e. providing the highest yield of the $C_8$ alcohol.

In a final step, an acid catalyzed etherification of the $C_8$ alcohol into desired final product $C_{16}$ ether is performed according to the overall reaction Scheme 1.

-continued

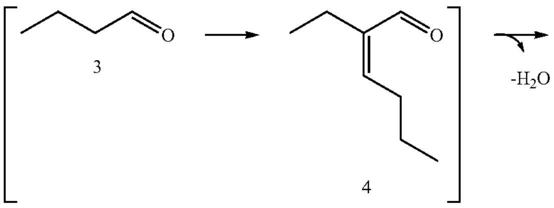

Scheme 1.
Overall integrated catalysis pathway for the conversion of simple aldehyde to higher value liquid fuel.

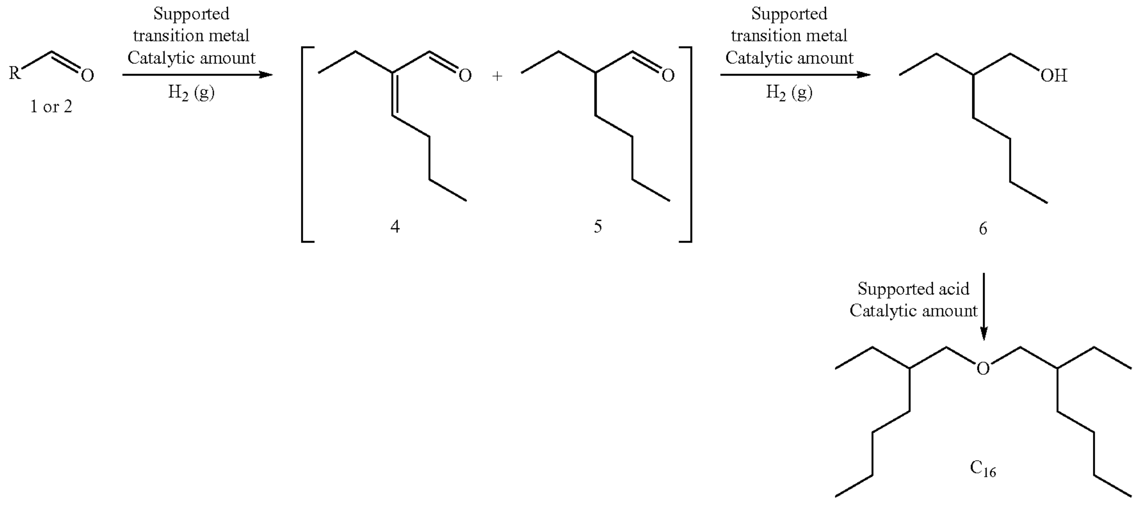

7

IUPAC: 3-(((2-ethylhexyl)oxy)methyl)heptane
CAS: 10143-60-9

The key intermediate in the process the branched $C_8$ aldehyde according to formula 5 below and controlling the formation thereof.

A one-pot conversion of acetaldehyde 1, or more preferably a croton aldehyde 2, into a branched valuable $C_8$ aldehyde according to formula 4 below and 5, is accomplished by a hydrogenation-condensation-hydrogenation in domino sequential reaction, according to reaction Scheme 2 below, via the in situ formation of intermediate butanal according to formula 3 below, followed by an additional cascade hydrogenation to form the branched $C_8$ alcohol 6.

Reaction scheme 2.
One-pot cascade reaction for the formation of $C_8$ alcohol.

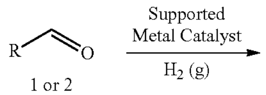

1 or 2

-continued

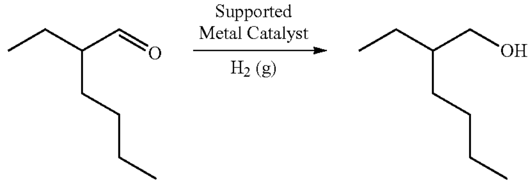

5 6

According to the invention an essential step in the inventive process is controlling the outcome products, i.e. the intermediary products, of the condensation reaction of croton aldehyde 2.

Therefore, in the inventive method croton aldehyde 2, is used as feedstock in the one-pot heterogeneous metal catalyzed synthesis of branched $C_8$ aldehyde 5 and branched alcohols 6 to achieve a high yield.

Transition metals such as Pd, Ni, Pt, Mo and Cu supported on aluminum and silica as heterogeneous catalysts were investigated for the catalytic conversion of acetaldehyde 1 and croton aldehyde 2 into $C_8$ branched alcohols 4.

Experiments

In initial experiments, an autoclave batch reactor was used as a reaction vessel to conduct this transformation and toluene were chosen as solvent for the one-pot experiments at different temperatures, according to reaction Scheme 3 below. The reaction conditions as disclosed in Scheme 3 were as follows 750 mmol/61 mL of croton aldehyde in 180 mL of solvent, C=4M, under indicated $H_2$ gas pressure and indicated temperature and time. The yields are based on GC-MS analysis.

Reaction scheme 3.
Suggested catalytic conversion of croton aldehyde 2

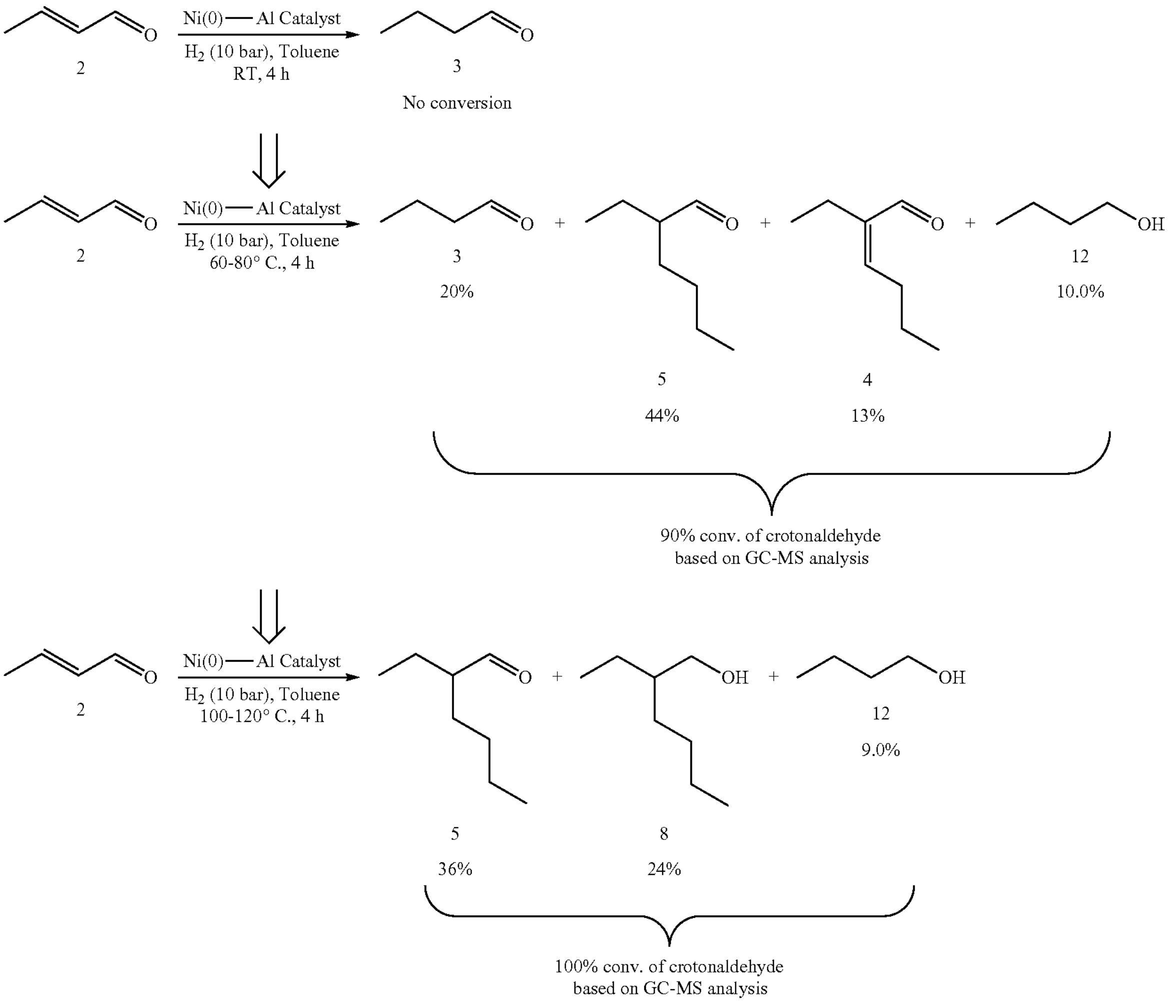

Furthermore, utilizing a Pd(0) metal as catalyst instead of the Ni(0) afford the branched aldehyde 5 as major product in one pot starting from the croton aldehyde 2, as feedstock, which is disclosed in reaction Scheme 4 below, where the reaction conditions were as follows: 750 mmol/61 mL of croton aldehyde in 180 mL of solvent, C=4M, under indicated $H_2$ gas pressure and indicated temperature and time. The yields based on GC-MS analysis.

Reaction scheme 4.
Using Pd(0) catalyst

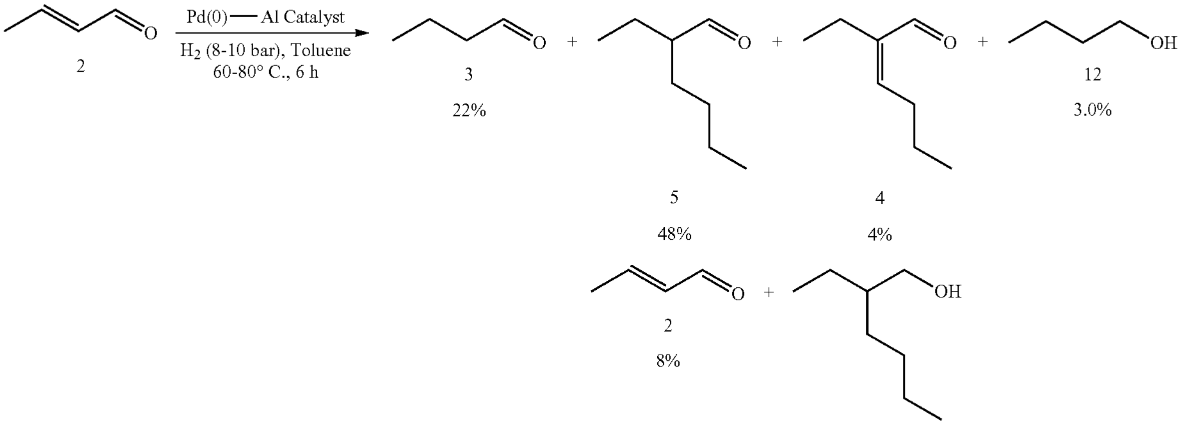

2

3
22%

5
48%

4
4%

12
3.0%

2
8%

6
2.0%

It was found that in order to sufficiently reduce the $C_8$, branched aldehyde 5, to branched alcohol 6 a Ni(0) based catalyst (catalyst TK-49 provided by HALDOR TOPSOE) preferably may be utilized.

In the second and separate step the target $C_{16}$ ether 7, is synthesized by an acid catalyzed etherification reaction.

As disclosed in reaction scheme 6 a sulfuric acid both as liquid and as heterogeneous supported on silica were applied successfully, utilizing a dean-stark equipment to remove the formed water as by product. The reaction conditions for the below reaction were: neat condition. The yields are based on GC-MS analysis.

Reaction scheme 6.
Acid catalyzed etherification reaction

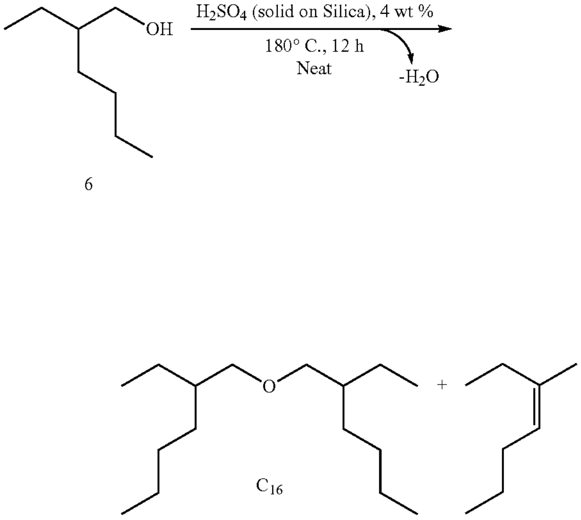

6

7

13

80:20

99% total conversion

-continued

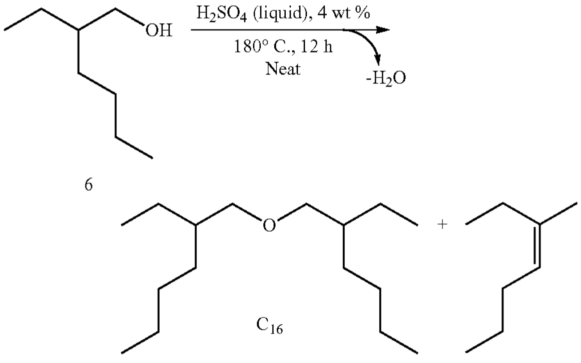

6

7

13

90:10

99% total conversion

Fuel Analysis

The di-(2-ethylhexyl) ether according to formula 7, was analyzed by Saybolt Sweden AB with regards to its properties as diesel fuel (with interpretation of test results as defined in ASTM D3244, EN 590, IP 367, ISO 4259 or GOST 33701).

The test results showed that the di-(2-ethylhexyl) ether according to formula 7 is suitable for use as diesel, since the density at 15° C. according to EN ISO 12185 was analyzed to be in the range of 800 to 845 $kg/m^3$, or more specifically in the range of 810 and 820 $kg/m^3$, and even more specifically to be 814.0 $kg/m^3$.

The analysis showed that the fuel product does however need further additives such as a lubricity improver to function properly in a combustion engine. The test results are disclosed in Table 1, below. The analysis discloses that the high value liquid fuel product may also be suitable for mixing with a fossil based diesel, since it has the same properties as a fossil fuel, e.g. with regards to density. It may also be useful for mixing with so called FAME products.

TABLE 1

Analysis of di(2-ethylhexyl) ether according to formula 7 as diesel

| NAME | | METHOD | UNIT | SPECS Min | SPECS Max | RESULT |
|---|---|---|---|---|---|---|
| Density at 15° C. | Q | EN ISO 12185 | $kg/m^3$ | 800/820 | 820/845 | 814.0 |
| Cloud point | | EN 23015 obs. | ° C. | | −16/0 | <−70 |
| Distillation | | EN ISO 3405 | | | | |
| initial boiling point | Q | | ° C. | 180 | | 217.8 |
| 10% Recovered | Q | | ° C. | | | 242.1 |
| 50% Recovered | Q | | ° C. | | | 257.7 |
| 90% Recovered | Q | | ° C. | | | 257.9 |
| 95% Recovered | Q | | ° C. | | 320 | 258.3 |
| Recovered at 180° C. | | | vol % | | 10 | <0.1 |
| Recovered at 250° C. | | | vol % | | 64.9 | 17.1 |
| Recovered at 350° C. | | | vol % | 85.0 | | 97.7 |
| Cetane Number | Q | EN ISO 5165 | — | 51.0 | | >73.6 |
| Oxidation Stability | | ISO 12205 | $g/m^5$ | | 25 | 25 |
| Lubricity | | ISO 12156 | μm | | 460 | 590 |
| Lubricity | | ISO 12156 | μm | | 460 | 480 |
| Appearance at 20° C. | | Visual | | | C & B | C&B |
| Aromatics Hydrocarbon | | EN 12916 | | | | |
| Poly Aromatics (di and higher) | | | mass % | | 8.0 | <0.5 |
| Ash | Q | EN ISO 6245 | mass % | | 0.010 | <0.001 |
| Carbon Residue Micro (10% bot.) | | ISO 10370/3405 | mass % | | 0.30 | <0.10 |
| Cetane Index | Q | ISO 4264 | — | 46.0 | | 61.7 |
| Cold Filter Plugging Point | Q | EN 116 | ° C. | | | −50 |
| Conductivity at 20° C. | | ASTM D 2624 | pS/m | 50 | | <10 |
| Copper Strip Corrosion 3 h at 50° C. | Q | EN ISO 2160 | — | | 1 | 1a |
| Flash point (PM) proc A | Q | EN ISO 2719 | ° C. | 56 | | 103.0 |
| Metals by ICP | | EN 16576 | | | | |
| Manganese (Mn) | | | mg/l | | 2.0 | <0.10 |
| Oxidation Stability | | EN 15751 | Hrs | 20 | | 0.3 |
| Sulphur | Q | EN ISO 20846 | mg/kg | | 10.0 | 221 |
| Total Contamination | | EN 12662 | mg/kg | | 24 | 1 |
| Water Kart Fischer | Q | ISO 12937 | mg/kg | | 200 | 168 |
| Kinematic Viscosity at 40° C. | | EN 16886 | $mm^2/s$ | 2.000 | 4.500 | 2.237 |
| FAME content | | EN 14078 | vol % | | 7.0 | <0.05 |

Modifications and other variants of the described embodiments will come to mind to one skilled in the art having benefit of the teachings presented in the foregoing description and associated drawings. Therefore, it is to be understood that the embodiments are not limited to the specific example embodiments described in this disclosure and that modifications and other variants are intended to be included within the scope of this disclosure. Furthermore, although specific terms may be employed herein, they are used in a generic and descriptive sense only and not for purposes of limitation. Therefore, a person skilled in the art would recognize numerous variations to the described embodiments that would still fall within the scope of the appended claims. As used herein, the terms "comprise/comprises" or "include/includes" do not exclude the presence of other elements or steps. Furthermore, although individual features may be included in different claims (or embodiments), these may possibly advantageously be combined, and the inclusion of different claims (or embodiments) does not imply that a combination of features is not feasible and/or advantageous. In addition, singular references do not exclude a plurality. Finally, reference signs in the claims are provided merely as a clarifying example and should not be construed as limiting the scope of the claims in any way.

The invention claimed is:

1. A one-pot method for producing a di(2-ethylhexyl) ether having a

7

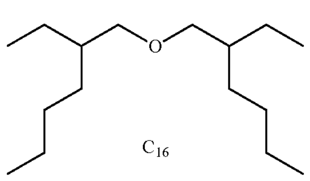

wherein the method comprises an integrated catalytic conversion of a $C_4$ croton aldehyde having the general formula 2:

2

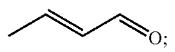

and wherein said the comprises acid catalyzed etherification of a branched $C_8$ alcohol having the general formula 6:

6

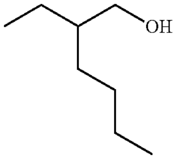

as prepared through the following reaction scheme:

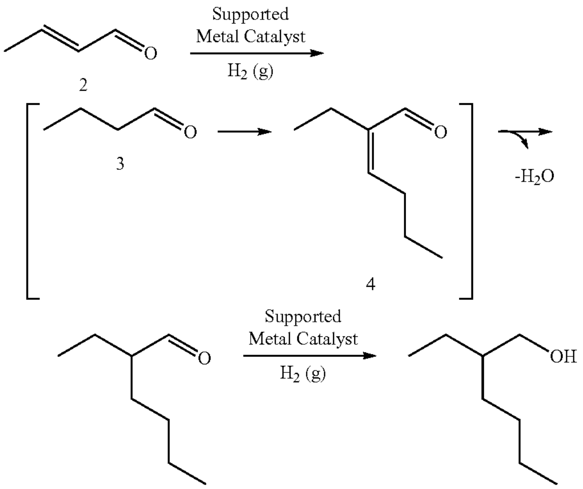

2 3 4 5 6 according to any one of the following reactions:

a) reacting compound 6 with 4 wt. % $H_2SO_4$ solid on silica at 180° C. for 12 h, neat, wherein water is removed, resulting in an 80:20 ratio of compound 7 and compound 13 having formula:

13

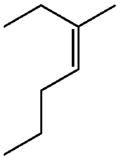

and 99% conversion of said compound 6:

and/or b) reacting compound 6 with 4 wt. % $H_2SO_4$ in a liquid at 180° C. for 12 h, neat, wherein water is removed, resulting in a 90:10 ratio of compound 7 and compound 13 and a 99% conversion of said compound 6 to form the di(2-ethylhexyl) ether.

2. The method of claim 1, wherein a Ni(0) metal catalyst is used in the step of producing the branched aldehyde according to formula 5.

3. The method of claim 1, wherein the integrated catalytic conversion of a $C_4$ croton aldehyde is performed under 10 bar $H_2$ at 100 to 120° C. during for 4 hours in a solvent.

4. The method of claim 1, wherein the integrated catalytic conversion of the $C_4$ croton aldehyde is performed in toluene as a solvent.

5. The method of claim 1, wherein the acid catalyzed etherification reaction is performed using a Dean-Stark equipment to remove water.

6. The method of claim 1, wherein the reduction of the branched $C_8$ aldehyde (5) to the branched $C_8$ alcohol (6) is performed using a Ni(0) based catalyst.

* * * * *